US010828009B2

(12) United States Patent
Binotto (10) Patent No.: US 10,828,009 B2
(45) Date of Patent: Nov. 10, 2020

(54) MONITORING BODY SOUNDS AND DETECTING HEALTH CONDITIONS

(71) Applicant: International Business Machines Corporation, Armonk, NY (US)

(72) Inventor: Alecio Pedro Delazari Binotto, São Paulo (BR)

(73) Assignee: International Business Machines Corporation, Armonk, NY (US)

(*) Notice: Subject to any disclaimer, the term of this patent is extended or adjusted under 35 U.S.C. 154(b) by 432 days.

(21) Appl. No.: 15/848,427

(22) Filed: Dec. 20, 2017

(65) Prior Publication Data

US 2019/0183450 A1    Jun. 20, 2019

(51) Int. Cl.
| | | |
|---|---|---|
| *A61B 5/00* | (2006.01) | |
| *A61B 7/02* | (2006.01) | |
| *H04R 1/40* | (2006.01) | |
| *A61B 7/04* | (2006.01) | |
| *G16H 30/20* | (2018.01) | |
| *G06T 19/00* | (2011.01) | |
| *G16H 50/20* | (2018.01) | |
| *H04R 3/00* | (2006.01) | |

(52) U.S. Cl.
CPC ............... *A61B 7/026* (2013.01); *A61B 7/04* (2013.01); *H04R 1/406* (2013.01); *G06T 19/006* (2013.01); *G06T 2207/30004* (2013.01); *G16H 30/20* (2018.01); *G16H 50/20* (2018.01); *H04R 3/005* (2013.01); *H04R 2201/40* (2013.01)

(58) Field of Classification Search
CPC .. A61B 7/026; A61B 5/72; A61B 7/04; H04R 1/406

USPC ......................................................... 600/586
See application file for complete search history.

(56) References Cited

U.S. PATENT DOCUMENTS

| | | |
|---|---|---|
| 6,139,505 A | 10/2000 | Murphy |
| 6,699,204 B1 | 3/2004 | Kehyayan |
| 6,790,183 B2 | 9/2004 | Murphy |
| 9,084,057 B2 | 7/2015 | Turqueti |
| 9,402,596 B1 | 8/2016 | Sheu |
| 2002/0183642 A1 | 12/2002 | Murphy |
| 2002/0183874 A1 | 12/2002 | McKinney |

(Continued)

FOREIGN PATENT DOCUMENTS

WO    WO2017120138    7/2017

OTHER PUBLICATIONS

Peter Mell, "The NIST Definition of Cloud Computing". Special Publication 800-145. Sep. 2011, pp. 1-7.

(Continued)

*Primary Examiner* — Max F Hindenburg
(74) *Attorney, Agent, or Firm* — Joseph Petrokaitis; Otterstedt, Wallace & Kammer, LLP (57) ABSTRACT

A method of monitoring body sounds using a sensor including an array of microphones, the method includes acquiring a first sound produced by certain physiology using the array of microphones of the sensor, identifying a source of the first sound, performing an automatic auscultation of the source using the first sound, wherein the automatic auscultation including matching the first sound to an acoustic model stored in a memory, wherein the acoustic model corresponds to a physiology, generating an image representing the physiology using an image library, and determining a health condition using the physiology and the image.

16 Claims, 5 Drawing Sheets

(56) References Cited

U.S. PATENT DOCUMENTS

| | | | |
|---|---|---|---|
| 2004/0267149 | A1 | 12/2004 | Kushnir |
| 2010/0049093 | A1* | 2/2010 | Galkin .................. A61B 6/502 |
| | | | 600/586 |
| 2011/0137209 | A1 | 6/2011 | Lahiji |
| 2012/0209131 | A1* | 8/2012 | Jones ...................... A61B 7/04 |
| | | | 600/528 |
| 2012/0209132 | A1* | 8/2012 | Jones ...................... G01S 5/18 |
| | | | 600/528 |
| 2012/0275621 | A1 | 11/2012 | Elko |
| 2013/0035610 | A1* | 2/2013 | Cromwell ............ A61B 5/7275 |
| | | | 600/586 |
| 2014/0371631 | A1 | 12/2014 | Fontana |
| 2015/0016641 | A1 | 1/2015 | Ugur |
| 2015/0201272 | A1 | 7/2015 | Wong |
| 2016/0206277 | A1 | 7/2016 | Bidichandani |
| 2016/0354053 | A1* | 12/2016 | Tsai .................... A61B 5/7253 |
| 2017/0161455 | A1* | 6/2017 | Grady .................. A61B 5/4848 |
| 2017/0180870 | A1 | 6/2017 | Hung |
| 2017/0215835 | A1 | 8/2017 | Sezan |
| 2017/0295429 | A1 | 10/2017 | Poletti |

OTHER PUBLICATIONS

Yun Li et al, "A Microphone Array System for Automatic Fall Detection," IEEE Transactions on Biomedical Engineering, vol. 59, No. 2, May 2012, pp. 1291-1301.

Turqueti, Marcos De Azambuja, "Acoustic MEMS array embedded in a scalable real-time data acquisition and signal processing platform," Illinois Institute of Technology, ProQuest Dissertations Publishing, Jul. 2010, pp. 1-132.

* cited by examiner

MONITORING BODY SOUNDS AND DETECTING HEALTH CONDITIONS

BACKGROUND

The present disclosure relates generally to methods and systems for detecting health conditions through auscultation.

Auscultation is the process of listening to internal sounds of the body, typically using a stethoscope or other sensor including a microphone and an amplifier. Auscultation is performed in the course of evaluating various conditions and functions, typically in connection with one or more of the circulatory system, the respiratory system, and the gastro-intestinal system. Auscultation is a skill that requires substantial clinical experience, a fine stethoscope sensor and good listening skills.

BRIEF SUMMARY

According to an embodiment of the present invention, a method of monitoring body sounds using a sensor comprising an array of microphones, the method including acquiring a first sound produced by certain physiology using the array of microphones of the sensor, identifying a source of the first sound, performing an automatic auscultation of the source using the first sound, wherein the automatic auscultation comprising matching the first sound to an acoustic model stored in a memory, wherein the acoustic model corresponds to a physiology, generating an image representing the physiology using an image library, and determining a health condition using the physiology and the image.

According to an embodiment of the present invention, a method includes acquiring a first sound produced by certain physiology using the array of microphones of the sensor, identifying a source of the first sound, performing an automatic auscultation of the source using the first sound, wherein the automatic auscultation comprising matching the first sound to an acoustic model stored in a memory, wherein the acoustic model corresponds to a physiology and a pathology, retrieving an image from an image library corresponding to the physiology, generating an augmented view of the image retrieved from the image library according to the pathology, and displaying the augmented view of the image.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

accurate images, generated using passive sensors, given a determined physiology; and     generating a diagnosis using acoustic models and generated imagery.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Embodiments of the present invention relate to a method for monitoring body sounds and detecting health conditions to support medical diagnosis. Auscultation, performed according to one or more embodiments of the present invention, augments other diagnostics performed during consultation. According to at least one embodiment, auscultation is performed as part of a homecare or remote care context.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 1:
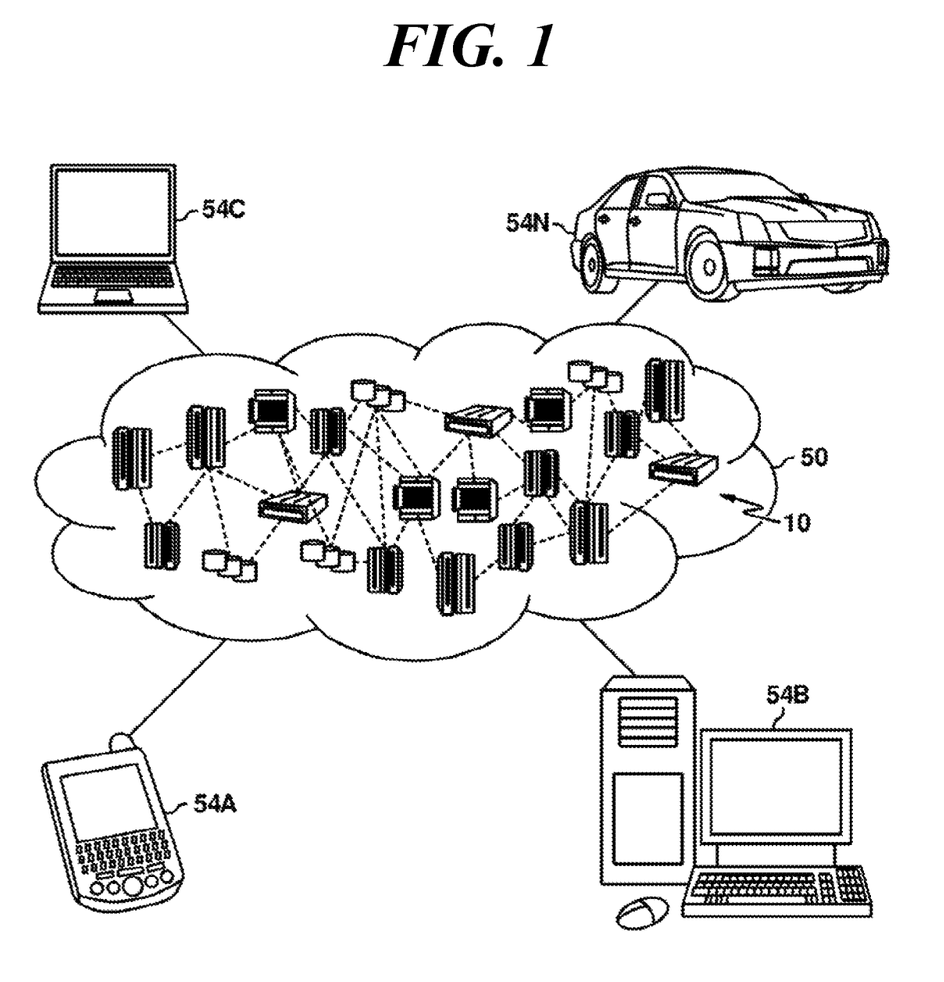
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
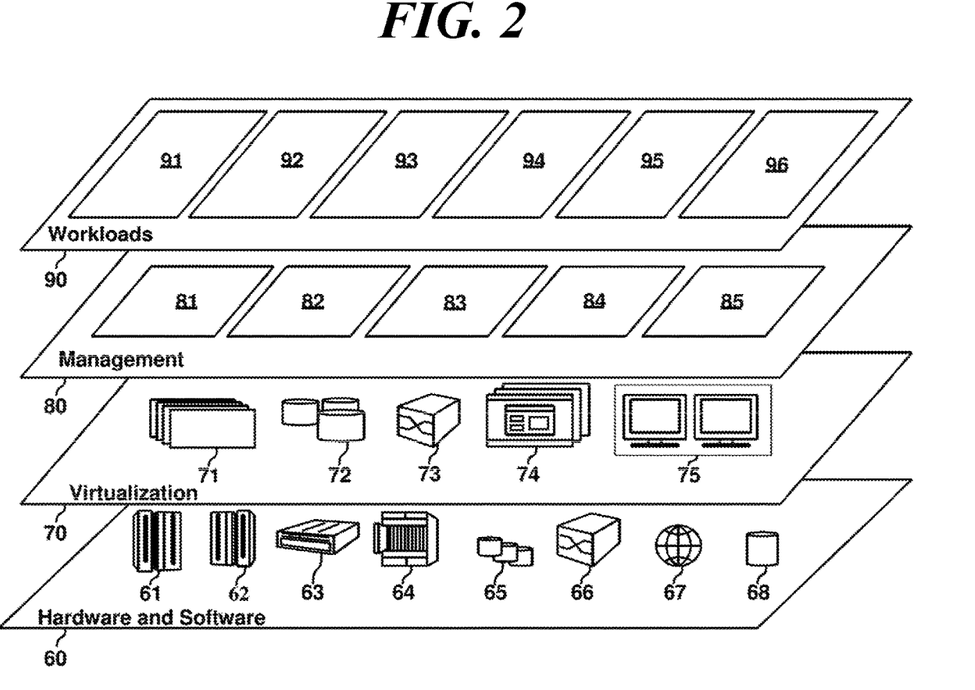
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and monitoring body sounds and detecting health conditions to support medical diagnosis 96. The monitoring and detection 96 can further include direct conversation between a patient and an artificial intelligence (AI) based virtual assistant (e.g., bot), which can provide, for example, wellness information.

According to one or more exemplary embodiments of the present invention, a method 300 (see FIG. 3) includes acquiring sounds 301 produced by certain physiology using a sensor comprising an array of microphones. In at least one embodiment the sensor is a MEMS (Microelectromechanical Systems) microphone array and includes one or more amplifiers. It should be understood that the present invention is not limited to MEMS devices, and other sensors are contemplated, for example, a Doppler device.

Figure 3:
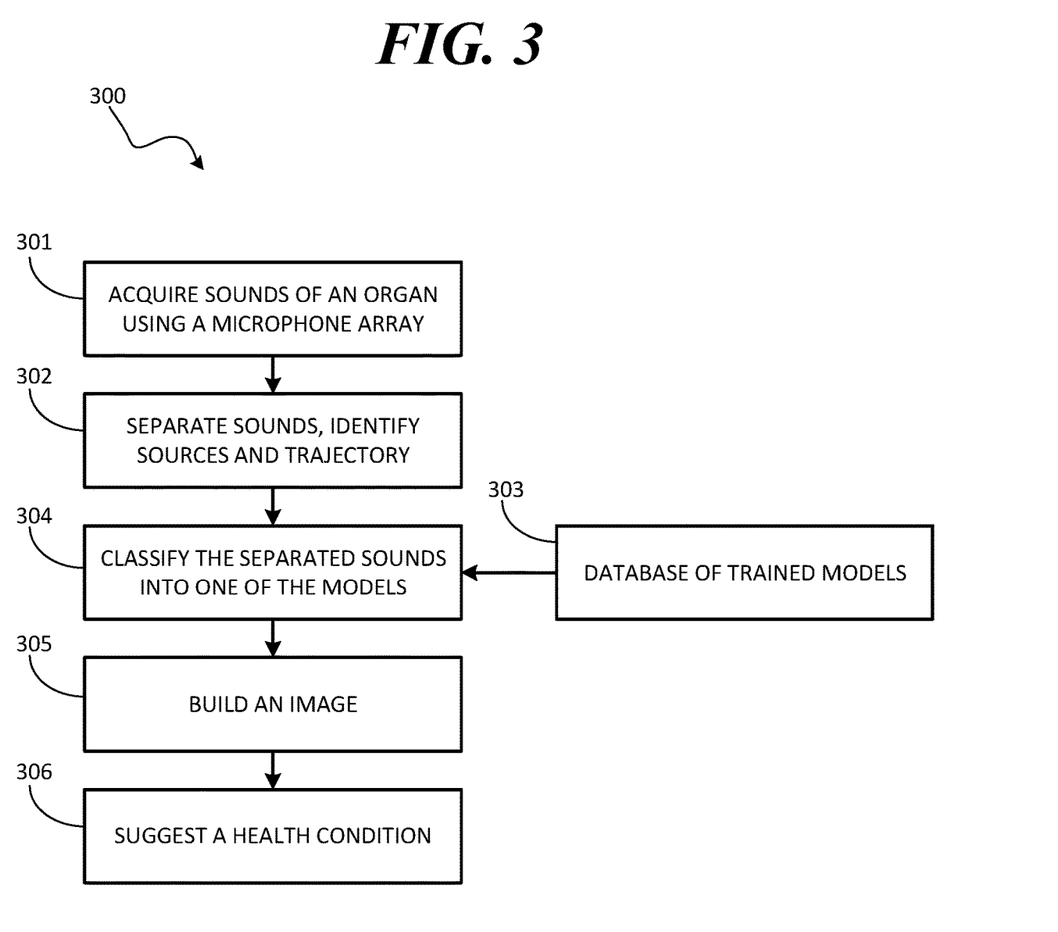
FIG. 3 is flow diagram of a method according to an embodiment of the present invention.

According to one or more exemplary embodiments of the present invention, the sensor is disposed on a circuit board, hard or flexible, formed of, for example, silicon. In the case of a flexible circuit board, a sensor is deformable and can be disposed on a patient's chest, below the left arm, and surrounding about 90 degrees of arc around the heart. It should be understood that different shaped sensors (rigid and/or flexible) can be adapted to specific applications, depending on the organs to be diagnosed.

According to one or more exemplary embodiments of the present invention, depending on the intensity of the sounds, the sensor device comprising an array of microphones can automatically and dynamically reconfigure to give more gain (or turn off/on) to certain microphones of the array, for example, microphones that are capturing louder or particular frequency/amplitude/phase sounds.

In one exemplary implementation, the sensor acquires heart sounds. These sounds are produced by specific cardiac events. A typical auscultation of the heart includes the identification of the first heart sound (S1) and second heart sound (S2), produced by the closing of the atrioventricular valves and semilunar valves, respectively. The third heart sound (S3) and fourth heart sound (S4) are related to the protodiastolic gallop and the presystolic gallop, respectively. These and other heart sounds can be described by various characteristics, including intensity (loudness), frequency (pitch), location (e.g., within the organ or body), quality and timing in the cardiac cycle. Similarly, the sounds of other physiology can be described by various characteristics.

The method further comprises separating the acquired sounds and identifying a source of each separated sound 302. Methods for sound separation and source identification are well-known in the art. The separation of the acquired sounds can be performed to, for example, separate sounds of interest from background noise, or to separate two sounds of interest from one-another (e.g., separating the S1 and S2 sounds, or separate a heart sound from a lung sound). It should be understood that the sound separation can use other information, such as observed imaging to separate (e.g., label) a certain sound.

According to at least one embodiment of the present invention, the source identification can include processing the sound to determine a trajectory of the separated sound and/or determine a location of the source using the array of microphones in a sound source localization method. According to another embodiment of the present invention, the source identification includes matching a recorded sound to a sound from a library of sounds to identify the source (e.g., determining that a certain sound emanates from the heart or the lungs); in this example the source identification is used in a labeling of an audio recording including the separated sounds (e.g., labeling certain heart sounds).

The method further includes training a knowledge base of acoustic models 303. According to at least one embodiment, the trained knowledge base is stored in a database accessible to a computer system configured to perform an automatic auscultation. Each of the acoustic models corresponds to a certain sound of a particular physiology, organ and/or area of the human body to one or more health conditions (e.g., Chronic Obstructive Pulmonary Disease (COPD), asthma, carotid stenosis, stroke, heart valves obstruction, a degree of healthy function, a likelihood of a given anomaly, temporomandibular joint (TMJ) disorders, etc.), such that the knowledge base maps sounds to physiology (e.g., organs and their parts, lung function, etc.), and more particularly functionality (e.g., of a certain heart valve, lung condition, skeletal conditions, etc.). One or more acoustic model targets a given organ. A set of acoustic models can be applied in evaluating certain physiology, one or more organs or systems of human body. According to one or more embodiments of the present invention, the set of acoustic models are used in configuring a computer system to perform an automatic health evaluation. According to at least one embodiment of the present invention, relationships between different audio signals and a health condition (e.g., the health state, disease state) of the patient supports a diagnosis.

According to an embodiment of the present invention, a new acoustic model can be learned from a set of labeled audio recordings stored in the knowledge base. Examples of audio recordings include recordings from digital stethoscopes, an array-based device (MEMS), etc. The knowledge base includes meta-data about a condition corresponding to each of the audio recordings. In this context, different sounds from a same physiology create a statistical representation of the sounds corresponding to the physiology. Statistical representations can be created for different physiologies, conditions, anomalies, etc.

According to an embodiment of the present invention, different models are trained with the same audio database. For example, two models may have different hyper-parameters during training with the same audio database. In another example, models of different types are trained with the same audio database, with a first model being based on a neural network and a second model being based on a SVM (Support Vector Machine), where supervised learning models with associated learning algorithms analyze data used for classification and regression analysis. Accordingly, through the training of different models for the same audio input, a robust statistical representation can be created for different physiologies, conditions, anomalies, etc.

According to an embodiment of the present invention, the discretized sounds are classified 304 compared to the acoustic models and one or more matches (i.e., to the acoustic models) are determined. According to an embodiment of the present invention, a match is determined by use of a Recurrent Neural Network (RNN) in which a sample input (x) (i.e., a recorded sound) is processed by a set of hidden weight matrices (A, W, . . . ) to produce an output (h), where the output (h) is the category of a health condition associated with the sample input.

Figure 5:
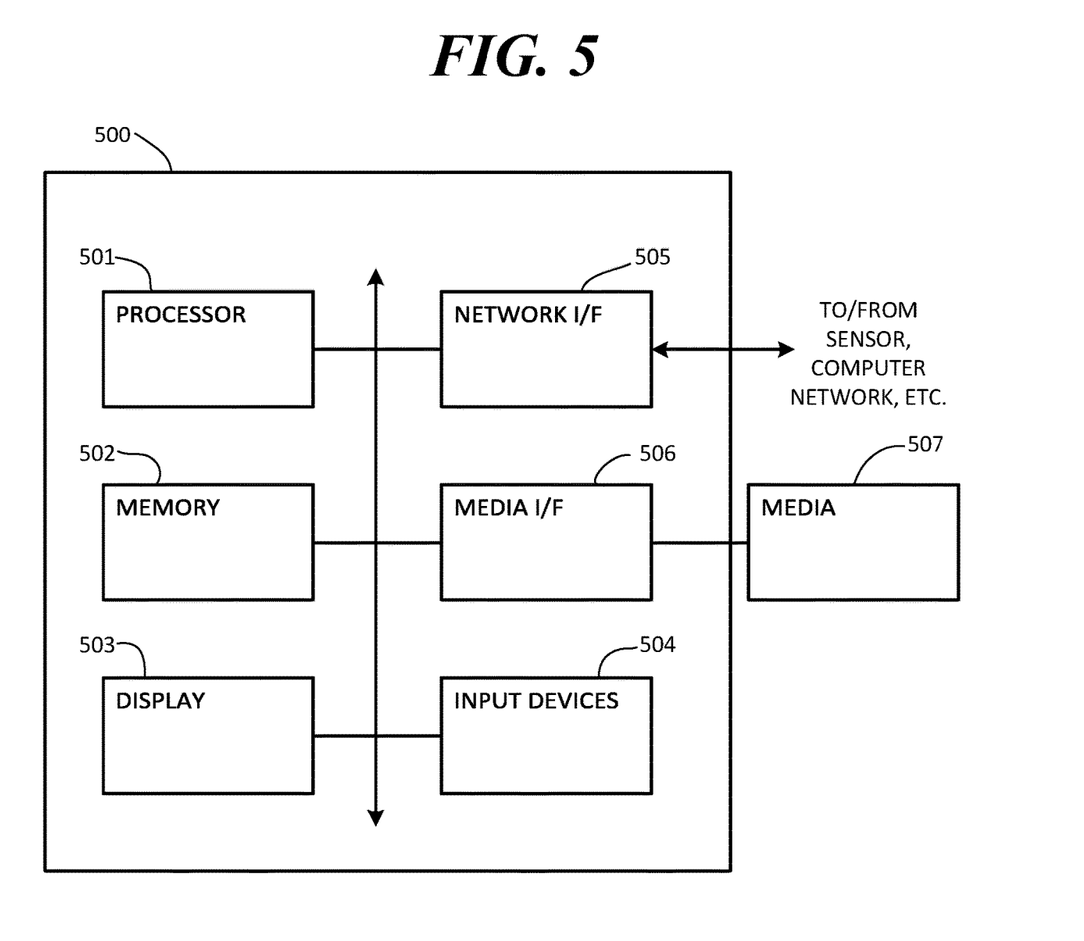
FIG. 5 is a block diagram depicting an exemplary computer system according to an exemplary embodiment of the present invention.

According to an embodiment of the present invention, an image (two-dimensional or three-dimensional) is generated that represents the output of the health condition 305. According to an exemplary embodiment of the present invention, with the microphones positioned at different locations relative to the array device, the source and trajectory can be determined. Further, sound dispersion between the source to the receiver device is determined. Using a plurality of microphones at different locations, the image can be formed (FIG. 5). According to an embodiment of the present invention, an image library of organs is used as a reference for the image construction. It should be understood that passive sensors (not an active sensor such as an ultrasound device that emits a signal and measures an echo) configured according to one or more embodiments of the present invention, enable the generation of an image with accurate layers/tissues inside human body. For example, with a plurality of microphones disposed around an object of interest, a source can be accurately determined. Additional data can be determined, such as dissipation of sound through the layers/tissues. According to an embodiment of the present invention, the image library is used to augment the generated image. The image library includes models (two-dimensional and/or three-dimensional) of organs or other physiology, for example, a particular blood vessel. According to an embodiment of the present invention, the condition (e.g., 30% of obstruction due to plaque in a carotid vein) is plotted in an identified model matching the determined source. For example, when the source of a certain sound is determined to be from a carotid artery, an image of the carotid artery is retrieved from the image library and augmented according to the specific data determined from the sounds (e.g., augmenting the retrieved image to show a 30% blockage of plaque). According to an embodiment of the present invention, an improved and accurate medical image can be constructed (e.g., by the merging of sounds acquisition and its dispersion through the layers/tissues and a three-dimensional model). According to an embodiment of the present invention, these images, generated from passive sensors, can be used in medical practice including diagnostics.

According to an embodiment of the present invention, a health condition is determined 306. According to at least one embodiment of the present invention, a confidence value is given for the output health condition, for example, outputting an indication of a certain anomaly with a 70% confidence. According to still another embodiment, the output gives the health condition with a severity, for example, a 40% carotid obstruction.

According to an embodiment of the present invention, the system updates the models using input from a physician in a continuous learning method. In the case of remote monitoring, an action can be suggested directly to the patient and/or nursing call center.

According to an exemplary embodiment of the present invention, in the case of a sensor adapted to diagnosis a carotid stenosis, a long rectangular-based microphone pattern can be used, one that disposes the microphones along the shape of a typical vein. In this example, the sensor includes microphones positioned in relatively unobstructed areas in which the sound of the fluid/blood can be captured with little interference from other tissue. It should be understood that obstructions in the vein (e.g., accumulated fats or plaque) generate turbulence in the blood flow that can be recorded by the sensor. Using the acoustic models, a flow rate sound can be separated and estimated to be mapped into an obstruction of a certain percentage.

According to an exemplary embodiment of the present invention, in the case of a sensor adapted to diagnosis heart valve, arrhythmia, the sensor comprises an array of microphones with a round pattern to capture the heart area. The sensor can be formed using a flexible circuit board to cover a three-dimensional area bellow the patient's arm. Frequency and phase sounds of valve problems are particular, as well as the sound of heart beating differently than an arrhythmia.

Figure 4:
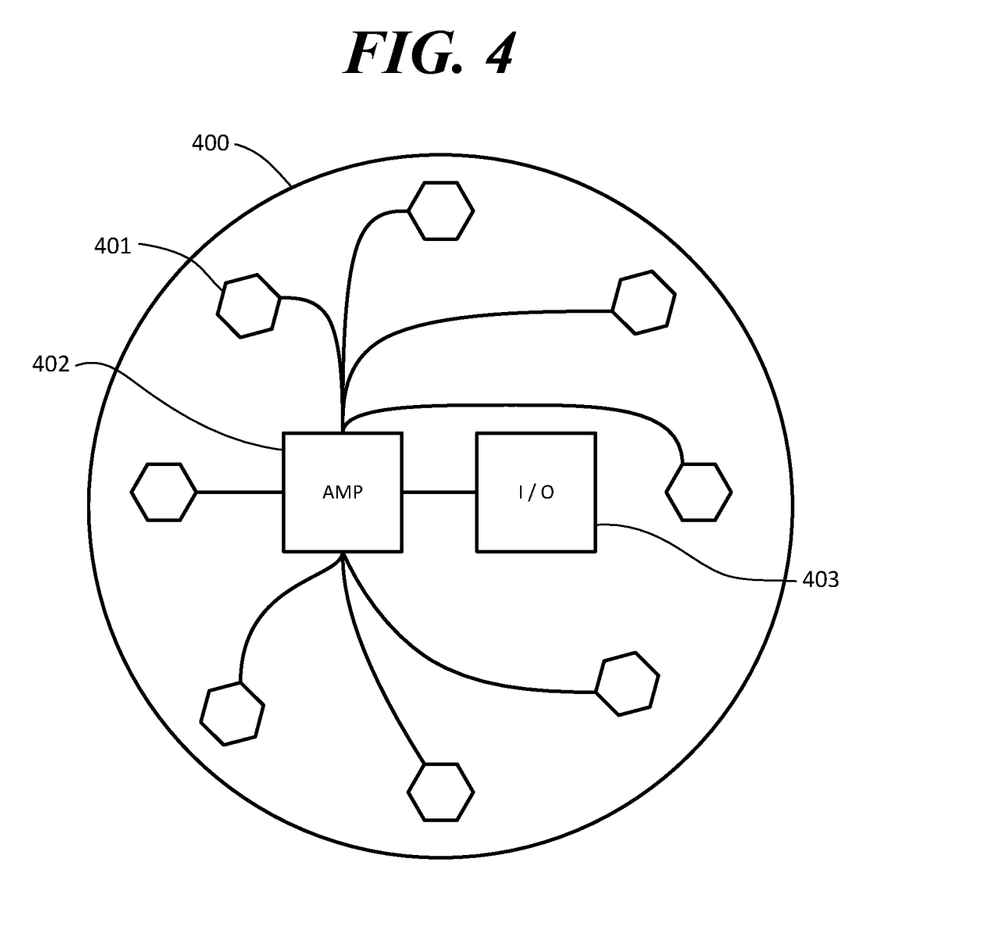
FIG. 4 is a diagram of a sensor according to an embodiment of the present invention.

According to an exemplary embodiment of the present invention, in the case of a sensor 400 (see FIG. 4) adapted to diagnosis COPD, the sensor 400 comprises an array of microphones 401 disposed in a round configuration/shape. The sensor 400 further includes an amplifier 402 connected to the microphones and an input/output (I/O) device 403 (e.g., wireless interface) for communicating with an external device such as a computer system (see for example, FIG. 5). The sensor 400 can include further components, such as a filter (not shown). According to an exemplary embodiment of the present invention, the computer system, using an output of the sensor 400, infers characteristics including lung/inspiratory (muscle function)/vital capacity, force vital capacity/expiratory volume, inspiratory/expiratory reserve volumes, etc.

It should be understood that particular arrangements of the microphones will depend on an application, particular frequencies (typically between about 20~500 Hz for a heart)/phases of a signal, etc.

According to one or more embodiments of the present invention, the system includes a display device for presenting a graphical user interface (GUI). In the case of a professional user, information related to the health condition is displayed. Such information can include a diagnosis such as a percentage of obstruction, a type of the heart problem (e.g., valve, arrhythmia), asthma (e.g., bronchitis), etc. In the case of a patient user, content related to education including wellness, exercises, health hints, or an action (e.g., seek immediate care) during remote monitoring.

According to one or more embodiments of the present invention, the sensor can be connected to a smartphone (e.g., by wired or wireless connection), where the smartphone executes an application running a data collection routine. The smartphone collects (e.g., by a wireless connection) data from a medical stethoscope (e.g., an electronic stethoscope) or spirometry. According to one or more embodiments of the present invention, the smartphone processes the collected data to output a diagnosis. According to at least one embodiment of the present invention, the smartphone communicates the data to a service, which performs the diagnosis. Furthermore, the smartphone can communicate with a smartwatch (e.g., using an available application program interface) or other device, which can include a GUI for presenting a diagnosis and/or consuming health hints/education content.

According to at least one embodiment of the present invention, the microphones (e.g., MEMS) of the sensor are micro components printed on a circuit board. Such microphones are portable and can be grouped to have a size or shape configured for a given wearer. According to at least one embodiment of the present invention, a composable device comprises a plurality of microphones, where individual microphones can be added or subtracted from the composable device. According to one or more embodiments of the present invention, the composable device is portable, and includes a processor for performing methods described herein. In at least one exemplary embodiment, the processing capabilities are performed by a connected (e.g., by wireless connection) smartphone.

According to at least one embodiment of the present invention, a device or sensor is embedded near an organ of interest, for example, in conjunction with a 1-lead electrocardiograph, giving precise confidence to the diagnosis.

According to at least one embodiment of the present invention, additional data is input to augment the diagnosis. For example, the smartphone execution the application connects to an electronic medical record to improve accuracy of the diagnosis, e.g., blood glucose (diabetes), weight, smoking, diet, cholesterol, height, abdominal circumference. The analysis can follow health protocols, like the Framingham risk protocols (risk calculators).

According to at least one exemplary embodiment of the present invention, the AI-based virtual assistant (bot) interacts with the physician to point out information based on papers or other sources of information, and/or with the patient to provide wellness and hints throughout a remote monitoring health program. This interaction can done over the cloud system, smartphone, directly through the bot, etc.

Recapitulation:

According to at least one embodiment of the present invention, a method of monitoring body sounds using a sensor comprising an array of microphones, the method including acquiring a first sound produced by certain physiology using the array of microphones of the sensor, identifying a source of the first sound, performing an automatic auscultation of the source using the first sound, wherein the automatic auscultation comprising matching the first sound to an acoustic model stored in a memory, wherein the acoustic model corresponds to a physiology, generating an image representing the physiology using an image library, and determining a health condition using the physiology and the image.

According to an embodiment of the present invention, a method includes acquiring a first sound produced by certain physiology using the array of microphones of the sensor, identifying a source of the first sound, performing an automatic auscultation of the source using the first sound, wherein the automatic auscultation comprising matching the first sound to an acoustic model stored in a memory, wherein the acoustic model corresponds to a physiology and a pathology, retrieving an image from an image library corresponding to the physiology, generating an augmented view of the image retrieved from the image library according to the pathology, and displaying the augmented view of the image.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a computer system for monitoring body sounds and detecting health conditions to support medical diagnosis. Further, a computer program product can include a tangible computer-readable recordable storage medium with code adapted to be executed to carry out one or more method steps described herein, including the provision of the system with the distinct software modules.

Referring to FIG. 5; FIG. 5 is a block diagram depicting an exemplary computer system configured to identify a specific food substance according to an embodiment of the present invention. The computer system shown in FIG. 5 includes a processor 501, memory 502, display 503, input device 504 (e.g., keyboard), a network interface (I/F) 505, a media I/F 506, and media 507, such as a signal source, e.g., camera, Hard Drive (HD), external memory device, etc.

In different applications, some of the components shown in FIG. 5 can be omitted. The whole system shown in FIG. 5 is controlled by computer readable instructions, which are generally stored in the media 507. The software can be downloaded from a network (not shown in the figures), stored in the media 507. Alternatively, software downloaded from a network can be loaded into the memory 502 and executed by the processor 501 so as to complete the function determined by the software.

The processor 501 may be configured to perform one or more methodologies described in the present disclosure, illustrative embodiments of which are shown in the above figures and described herein. Embodiments of the present invention can be implemented as a routine that is stored in memory 502 and executed by the processor 501 to process the signal from the media 507. As such, the computer system is a general-purpose computer system that becomes a specific purpose computer system when executing routines of the present disclosure.

Although the computer system described in FIG. 5 can support methods according to the present disclosure, this system is only one example of a computer system. Those skilled of the art should understand that other computer system designs can be used to implement embodiments of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of monitoring body sounds using a sensor comprising an array of microphones, the method comprising:
  acquiring a first sound produced by certain physiology using the array of microphones of the sensor;
  identifying a source of the first sound;
  performing an automatic auscultation of the source using the first sound, wherein the automatic auscultation comprising matching the first sound to an acoustic model stored in a memory, wherein the acoustic model corresponds to a physiology;

generating an image representing the physiology using an image library; and determining a health condition using the physiology and the image.

2. The method of claim 1, further comprising separating the first sound from a second sound.

3. The method of claim 1, wherein the acoustic model corresponds to a pathology of the physiology.

4. The method of claim 1, wherein determining the health condition further comprises outputting a confidence value for the health condition.

5. The method of claim 1, further comprising training the acoustic model using a labeled audio recording.

6. A non-transitory computer readable medium comprising computer executable instructions, which when executed by a computer, cause the computer to perform a method of monitoring body sounds using a sensor comprising an array of microphones, the method comprising:

acquiring a first sound produced by certain physiology using the array of microphones of the sensor, wherein the sensor is a passive sensor;

identifying a source of the first sound;

performing an automatic auscultation of the source using the first sound, wherein the automatic auscultation comprising matching the first sound to an acoustic model stored in a memory, wherein the acoustic model corresponds to a physiology;

generating an image representing the physiology using an image library; and determining a health condition using the physiology and the image.

7. The computer readable medium of claim 6, further comprising separating the first sound from a second sound.

8. The computer readable medium of claim 6, wherein the acoustic model corresponds to a pathology of the physiology.

9. The computer readable medium of claim 6, wherein determining the health condition further comprises outputting a confidence value for the health condition.

10. The computer readable medium of claim 6, further comprising training the acoustic model using a labeled audio recording.

11. A method comprises:

acquiring a first sound produced by certain physiology using an array of microphones of the sensor;

identifying a source of the first sound;

performing an automatic auscultation of the source using the first sound, wherein the automatic auscultation comprising matching the first sound to an acoustic model stored in a memory, wherein the acoustic model corresponds to a physiology and a pathology;

retrieving an image from an image library corresponding to the physiology;

generating an augmented view of the image retrieved from the image library according to the pathology; and displaying the augmented view of the image.

12. The method of claim 11, further comprising separating the first sound from a second sound.

13. The method of claim 11, further comprising:

determining a health condition using the augmented view of the image; and outputting a confidence value for the health condition.

14. The method of claim 11, further comprising training the acoustic model using a labeled audio recording.

15. The method of claim 1, wherein generating the image representing the physiology using the image library comprises:

retrieving a reference image from the image library corresponding to the physiology;

generating an augmented view of the reference image retrieved from the image library according to the first sound acquired by the array of microphones; and displaying the augmented view of the image.

16. The computer readable medium of claim 6, wherein generating the image representing the physiology using the image library comprises:

retrieving a reference image from the image library corresponding to the physiology;

generating an augmented view of the reference image retrieved from the image library according to the first sound acquired by the array of microphones; and displaying the augmented view of the image.

* * * * *